(12) United States Patent
Tamazawa

(10) Patent No.: US 7,247,672 B2
(45) Date of Patent: Jul. 24, 2007

(54) LIQUID NON-AQUEOUS DISPERSION AND PROCESS FOR PRODUCING THE SAME

(75) Inventor: Mitsuo Tamazawa, Matsudo (JP)

(73) Assignee: Taisei Chemical Industries, Ltd., Tokyo (JP)

( * ) Notice: Subject to any disclaimer, the term of this patent is extended or adjusted under 35 U.S.C. 154(b) by 644 days.

(21) Appl. No.: 10/314,412

(22) Filed: Dec. 9, 2002

(65) Prior Publication Data

US 2004/0109834 A1 Jun. 10, 2004

(51) Int. Cl.
*C08L 83/07* (2006.01)
(52) U.S. Cl. ...................................... 524/588; 526/279
(58) Field of Classification Search .................... None
See application file for complete search history.

(56) References Cited

U.S. PATENT DOCUMENTS 5,061,481 A * 10/1991 Suzuki et al. ................. 424/63

FOREIGN PATENT DOCUMENTS

| JP | 2-247110 | | 10/1990 |
| JP | 8-269332 | | 10/1996 |
| JP | 2000-063225 | | 2/2000 |
| JP | 2002-255748 | * | 9/2002 |

* cited by examiner

*Primary Examiner*—Kuo-Liang Peng
(74) *Attorney, Agent, or Firm*—Paul E. White; Manelli Denison & Selter PLLC

(57) ABSTRACT

A liquid non-aqueous dispersion including a silicone oil and a copolymer dispersed therein, the copolymer including (A) at least one radical polymerizable macromonomer containing dimethyl polysiloxane, and (B) at least one radical copolymerizable monomer with the macromonomer (A), which includes at least one (meth)acrylate monomer and optionally at least one vinyl monomer. This liquid non-aqueous dispersion has excellent water resistance, oil resistance and adhesive properties, and when used as a component of cosmetics, it can meet both requirements for long lasting make-up and good feeling of use of cosmetics.

2 Claims, No Drawings

LIQUID NON-AQUEOUS DISPERSION AND PROCESS FOR PRODUCING THE SAME

BACKGROUND OF THE INVENTION

The present invention relates to a liquid non-aqueous dispersion having a copolymer dispersed in a silicone oil, and a process for producing such a dispersion.

Various types of polymers have been used as one of base materials of cosmetics for the purpose of providing cosmetics with such functions as water resistance, oil resistance and adhesion to the skin and making cosmetics keep long. For example, high-molecular weight polymers such as polyvinyl alcohol, polyvinyl pyrrolidone, polyvinyl acetate, acrylic ester-based resins, nitrocellulose, alkyd resins, polyamide resins, methoxyethylene/maleic anhydride copolymer and alkanolamine solution of acrylic resins have been used as a base material of cosmetics such as makeup cosmetics, hair cosmetics, nail cosmetics and basic cosmetics.

Cosmetics containing these polymers are indeed improved in durability, but since the coating film formed on the human bodies by application of the cosmetics containing these polymers becomes a continuous film in which the polymer chains are intertwined with each other without a special design, these cosmetics have the problem that they are rather awkward to be applied by users because the cosmetics give the users such an unpleasant feeling that the human bodies are pulled by the coating film formed. Thus, it was hardly possible to increase the polymer content in the cosmetic formulations, so that a cosmetic material excellent in long-keeping quality has not been obtained.

Under these circumstances, development of a polymer useful for a cosmetic material that can provide cosmetics having good feeling of use and excellent long-keeping quality has been desired.

Use of silicone-acrylic resins as such a polymer has been proposed as a solution to the above problem, and many researches have been made for the improvement of spread, removal of rough feeling and other disagreeable qualities of cosmetics by taking advantage of slip properties of the silicone component.

For instance, JP-A-2-247110 tries to satisfy both requirements for durability and good feeling of use of cosmetics by compounding a silicone-acrylic graft polymer. According to this method, however, when cosmetics blended with the polymer are applied, the coating film formed on the surface of the human body becomes a continuous film in which the polymer chains are intertwined with each other because the polymer used is the one which has been synthesized by a solution polymerization technique. Therefore, feeling of use of these cosmetics was still unsatisfactory, and there was also a restriction on the amount of polymer that can be compounded.

JP-A-8-269332 proposes to blend in cosmetics a non-aqueous resin dispersion prepared by dispersing an acrylic polymer in a hydrophobic medium such as silicone oil by using a silicone-based dispersant resin. In this case, however, as the dispersion is produced by a two-step polymerization method using a large quantity of a high-molecular weight silicone-based dispersant resin which has been previously produced by polymerization, the product assumes a state of solution in which the silicone moiety of the silicone-based dispersant resin is dissolved in a hydrophobic medium, and the obtained dispersion does not become a perfect dispersion system and is highly viscous. Further, since the coating film formed after application of cosmetics is a continuous film in which silicone segments of the silicone moiety of the silicone-based dispersant resin are similarly intertwined with each other, feeling of use of cosmetics is not improved.

Thus, for a material of cosmetics, it is desirable to blend such a polymer dispersion that polymer chains existed on the surfaces of the polymer particles are not intertwined with each other and polymer particles stand in a two dimensional array on the surface of the human body as a film when applying the cosmetics, but there has yet been available no polymer dispersion that can meet the requirement for providing cosmetics with good feeling of use.

Accordingly, an object of the present invention is to provide a polymer dispersion capable of offering cosmetics which have the above-mentioned properties, good water resistance, oil resistance and adhesive qualities to help make-up last longer, can be applied with no resistance, and give good sense of use without causing a disagreeable feeling that the surface of the human body after application of cosmetics is pulled by the coating film formed.

It is also an object of the invention to provide the polymer dispersion in the form of a liquid non-aqueous preparation.

SUMMARY OF THE INVENTION

The present inventors have found that each of the following features have contributed to the deterioration of the feeling of use of cosmetics containing a high-molecular weight polymer:

1) In the solution type polymers, the polymers form such a state that they are dissolved in a solution, while the polymer chains are intertwined with each other, so that the coating film formed after application of cosmetics is a continuous film in which the polymer chains still remain intertwined with each other;

2) In the emulsion type polymers, although the polymer particles are dispersed in a solution, fusion of the polymer particles takes place when a coating film is formed on application of cosmetics, so that the formed coating film assumes a state where the polymer chains are intertwined with each other.

The present inventors have also found that in order to solve the above problems causes, it is essential that:

1) The polymer particles remain dispersed in a solution; and

2) Even after a coating film has been formed by application of cosmetics, the polymer chains on the particle surfaces are not intertwined between the dispersed polymer particles, and the polymer particles aggregate while physically maintaining their shape.

Various methods, such as ICI method (JP-B-40-23350), Cook Paint method (JP-B-47-21581) and Ford method (JP-B-47-8537), have been known for producing a non-aqueous dispersed polymer for obtaining a desired dispersion condition.

In the above methods, there are first synthesized the components soluble in hydrocarbons in a hydrocarbon-based hydrophobic solvent, and then the components insoluble in hydrocarbons are graft polymerized to attain stabilization of dispersion. However, as a result of investigations by the present inventors, it has been found that:

1) These methods are complicated, and it is difficult to prepare a high-concentration solution by these methods;

2) There is a limitation on composition for obtaining a stabilized dispersion.

3) In these methods, stabilized dispersion is acquired by arranging the soft components soluble in hydrocarbons on the dispersed particle surfaces, so that the formed coating film is a continuous film in which the polymer chains are intertwined with each other.

Further studies on these problems by the present inventors have led to the attainment of the present invention.

Thus, the present invention provides a liquid non-aqueous polymer dispersion comprising a silicone oil and a copolymer dispersed therein, said copolymer comprising (A) 1 to 20% by weight of at least one radical polymerizable macromonometer containing dimethyl polysiloxane, which is represented by the following formula (1):

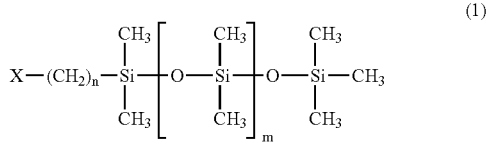
(1)

(wherein X represents a radical polymerizable group, n is an integer of 1 to 10, and m is an integer of 3 to 300), and (B) 99 to 80% by weight of at least one radical copolymerizable monomer with said component (A), which comprises at least one (meth)acrylate monomer and optionally at least one vinyl monomer.

In the polymer dispersion of the present invention, dimethyl polysiloxane groups are dispersed in a silicone oil in such a state that they are arranged on the copolymer particle surfaces, so that when this dispersion is blended in a cosmetic preparation and the resulting cosmetic is applied on the skin, a coating film is formed in which the dispersed copolymer particles aggregate to each other. Thus, incorporation of said dispersion in cosmetics makes it possible to form a coating film having excellent water and oil resistance, easy to apply and free of any disagreeable feeling on application.

DETAILED DESCRIPTION OF THE INVENTION

As mentioned above, the liquid non-aqueous dispersion of the present invention is a dispersion having a copolymer dispersed in a silicone oil. The copolymer used in the present invention is one obtained by copolymerizing (A) at least one radical polymerizable macromonomer containing dimethyl polysiloxane and (B) at least one radical copolymerizable monomer with said macromonomer.

The silicone oils usable in the present invention include dialkyl polysiloxanes such as dimethyl polysiloxane, diethyl polysiloxane and dibutyl polysiloxane; alkylphenyl polysiloxanes such as methylphenyl polysiloxane and ethylphenyl polysiloxane; cyclic dialkyl polysiloxanes such as cyclic dimethyl polysiloxane, cyclic diethyl polysiloxane and cyclic dibutyl polysiloxane; and cyclic alkylphenyl polysiloxanes such as cyclic methyphenyl polysiloxane, cyclic ethylphenyl polysiloxane and cyclic butylphenyl polysiloxane. Modified polysiloxanes such as amino-modified polysiloxanes, polyether-modified polysiloxanes and alkyl-modified polysiloxanes may be also used. These silicone oils may be used either alone or as a combination of two or more of them according to the purpose of the cosmetic.

The radical polymerizable macromonomer (A) containing dimethyl polysiloxane is represented by the following formula (1):

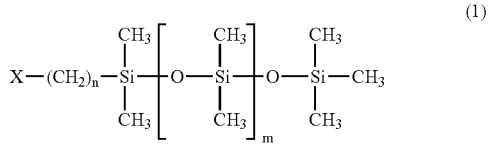
(1)

(wherein X represents a radical polymerizable group, n is an integer of 1 to 10, and m is an integer of 3 to 200).

Examples of the radical polymerizable groups represented by X in the above formula are acryloxy group, methacryloxy group, styryl group, allyl group, vinylbenzene group, vinyl ether group, acrylamide group, vinylalkylsilyl group, and vinyl ketone group.

Examples of the macromonomer (A) are dimethylpolysiloxypropylacrylic ester, dimethylpolysiloxypropylmethacrylic ester, dimethylpolysiloxypropylbenzyl ether, dimethylpolysiloxypropylacrylamide, and dimethylpolysiloxypropionic vinylbenzilate. Among them, dimethylpolysiloxypropylacrylic ester and dimethylpolysiloxypropylmethacrylic ester are particularly preferred.

The number-average molecular weight of macromonomer (A) is 1,000 to 100,000, preferably 2,000 to 50,000 in terms of polystyrene value measured by GPC. When it is less than 1,000, dispersion stability is unsatisfactory, and when it exceeds 100,000, the produced dispersion becomes too high in viscosity. These macromonomers can be used either alone or as a combination of two or more.

Macromonomer (A) is a component dissolved in a silicone oil, and its amount is 1 to 20% by weight, preferably 2 to 15% by weight of the total amount of monomers. When its amount exceeds 20% by weight, the obtained copolymer may be dissolved in silicone oil, making cosmetics less convenient to apply. Cosmetics may also have stickiness derived from the macromonomer. On the other hand, when the amount of macromonomer (A) is less than 1% by weight, no stabilized dispersion can be obtained.

Radical copolymerizable monomer (B) with the macromonomer (A) contains at least one (meth)acrylate monomer as an essential component and may optionally contain at least one vinyl monomer copolymerizable with the (meth)acrylate monomer.

The (meth)acrylate monomers are different from the macromonomers (A) in polarity, so that in the present invention it is possible to use ordinary (meth)acrylates without restrictions. Therefore, in the polymerization process in a silicone oil having strong hydrophobic properties, the (meth)acrylate monomers having relatively high polarity as compared with the silicone oil, namely, hydrophilic monomers are buried in the core part of the polymer particle in the non-aqueous dispersion. Such (meth)acrylate monomers may be used either alone or as a combination of two or more. Examples of these (meth)acrylate monomers include alkyl (meth) acrylates such as methyl (meth)acrylate, ethyl (meth)acrylate, N-butyl (meth)acrylate, 2-ethylhexyl (meth)acrylate, stearyl (meth)acrylate, benzyl (meth)acrylate and cyclohexyl (meth)acrylate; hydroxyl group-containing (meth) acrylates, for example, hydroxyalkyl (meth)acrylates such as 2-hydroxyethyl (meth)acrylate and 2-hydroxypropyl (meth)acrylate; carboxyl group-containing monomers such as acrylic acid, methacrylic acid, crotonic acid, itaconic acid, fumaric acid, maleic acid and their half esters; phosphate group-containing (meth)acrylates such as LIGHT ESTER PA and LIGHT ESTER PM (both being produced by Kyoei Chemical Co., Ltd.): basic (meth)acrylates such as N,N-dimethylaminoethyl (meth)acrylate and N,N-diethylaminoethyl (meth)acrylate; epoxy group-containing (meth)acrylates such as glycidyl (meth)acrylate; N-alkoxy-substituted amides such as N-methoxymethylol (meth)acrylamide and N-butoxymethylol (meth)acrylamide; and carbonyl-containing monomers such as diacetone acrylamide and acetoacetoxyethyl methacrylate.

Examples of the vinyl monomer copolymerizable with the (meth)acrylate monomer, which is an optional component, include aromatic vinyls such as styrene, acephamethylstyrene and vinyltoluene; unsaturated nitriles such as (meth) acrylonitrile; and vinyl esters such as vinyl acetate and vinyl propionate. Further, polyfunctional vinyl monomers such as divinylbenzene, trimethylolpropane tri(meth)acrylate, ethylene glycol di(meth)acrylate, etc., may be used as an optional component together with a (meth)acrylate monomer. These monomers may be used either alone or as a combination of two or more of them.

The amount of monomer (B) is 99 to 80% by weight, preferably 98 to 85% by weight of the total amount of monomers.

Glass transition temperature (Tg) of the copolymer consisting of macromonomer (A) and monomer (B) is −30 to 80° C., preferably 10 to 50° C. If Tg is below −30° C., the coating film is not provided with sufficient strength, and if Tg is above 80° C., the film forming properties are poor and film adhesion is unsatisfactory.

The liquid non-aqueous dispersion according to the present invention can be obtained by subjecting macromonomer (A) and monomer (B) to one-step radical polymerization in a silicone oil such as mentioned above in the presence of a radical polymerization initiator without using any dispersion stabilizer.

As the radical polymerization initiator, any of those commonly employed for ordinary radical polymerization can be used, the examples thereof being azo compounds such as 2,2-azobisisobutyronitrile, 2,2-azobis(2,4-dimethylvaleronitrile), 2,2-azobis(4-methoxy-2,4-dimethylvaleronitrile) and dimethyl 2,2-azobisisobutyrate; and organic peroxides such as lauroyl peroxide, t-butyl peroxide, dicumyl peroxide, t-butylperoxy-2-ethylhexanoate and benzoyl peroxide.

The amount of polymerization initiator is preferably 0.01 to 5% by weight, more preferably 0.1 to 2% by weight of the total amount of monomers.

A chain transfer agent such as mercaptoacetic acid, mercaptopropionic acid, 2-propanethiol, 1-butanethiol, 2-mercaptoethanol, ethyl mercaptoacetate, thiophenol, 2-naphthalenethiol, dodecylmercaptan, etc., may be used in polymerization for the adjustment of molecular weight.

The polymerization reaction is usually carried out in a silicone oil at temperatures ranging from 30 to 180° C., preferably 80 to 150° C. The reaction can be completed in about 5 to 10 hours by adding or adding dropwise continuously macromonomer (A), monomer (B), polymerization initiator and other necessary substances to the silicone oil under the above conditions.

It is considered that when macromonomer (A) and monomer (B) are subjected to radical copolymerization in a silicone oil, with macromonomer (A) being dissolved in the silicone oil in appearance, monomer (B) is increased in molecular weight and insolubilized in the silicone oil as the polymerization reaction proceeds, thereby causing a phase transformation with dimethyl polysiloxane coming on the outside and the acrylic component staying on the inside in a rounded form. Thus, such a dispersion structure that the copolymer of macromonomer (A) and monomer (B) is dispersed in the silicone oil can be formed.

Therefore, dispersion stability and particle size are decided by changing the copolymer composition of macromonomer (A) and monomer (B), and it is possible to control the particle size and molecular weight of the copolymer dispersed in the silicone oil by adjusting the kind of monomer (B), polymerization reaction temperature, the kind and amount of polymerization initiator (catalyst) and the way of addition of the monomers.

The weight-average molecular weight of the copolymer dispersed in silicone oil is preferably within the range of 5,000 to 500,000, particularly 10,000 to 100,000, in terms of polystyrene value measured by GPC. If the molecular weight is less than 5,000, the product becomes sticky, and if the molecular weight exceeds 500,000, the product falls short of film forming properties and lowers in adhesion.

The particle size of the copolymer dispersed in silicone oil is preferably from 0.05 to 2.0 μm, particularly 0.1 to 0.8 μm for obtaining a coating film having desired transparency. When the particle size exceeds 2.0 μm, the dispersed particles of the copolymer become unstable and also transparency of the coating film deteriorates.

The dispersed particles of the copolymer in silicone oil, obtained in the manner described above, have such a structure that polydimethylsiloxane is existed on their surfaces, so that in addition to excellent water resistance, oil resistance and adhesive properties attained by the copolymer itself, because of low viscosity, the product can spread well even in the course of drying, is easy to apply and gives a pleasant feeling on application. Further, since the formed coating film is free of intertwining of molecular chains, the skin is not bothered by an uncomfortable feeling due to stretch. Thus, the liquid non-aqueous dispersion of the present invention has the advantages which cannot be found in the conventional liquid non-aqueous dispersions.

As explained above, by incorporating the liquid non-aqueous dispersion of the present invention in a cosmetic base, it is possible to satisfy both requirements for long lasting make-up and good feeling of use of cosmetics which could not be achieved by use of the conventional polymers and polymer dispersions. The liquid non-aqueous dispersion of the present invention, therefore, can be used widely as a component material for a variety of cosmetics, for example, make-up cosmetics such as foundation, powder, cheek rouge, eye shadow and mascara, hair cosmetics such as hair color, hair spray, hair foam and hairdye, nail cosmetics such as nail cream and nail enamel, lip cosmetics such as rouge and lip cream, eyeliner cosmetics, basic cosmetics such as cream, milky lotion (emulsion) and lotion, and cleansing cosmetics such as shampoo and rinse.

DESCRIPTION OF PREFERRED EMBODIMENTS

The present invention will be described in further detail by showing the following examples, but, the examples are merely intended to be illustrative and not to be construed as limiting the scope of the invention.

Preparation of Silicone Oil-dispersed Polymer Solution

EXAMPLE 1

400 g of a commercial silicone oil KF-995 (decamethylcyclopentasiloxane produced by Shin-Etsu Chemical Industries Co., Ltd.) was added to a reactor equipped with a thermometer, a reflux condenser, a stirrer and a dropping funnel, and after replacing the reactor atmosphere with nitrogen gas, the silicone oil was heated and maintained at 120° C. To this, a mixture of 336 g of methyl methacrylate (MMA), 224 parts of 2-ethylhexyl acrylate (2EHA), 40 g of a commercial silicone macromonomer FM-0721 (polydimethylsiloxypropylacrylic ester; mono-terminal SAILAPLANE produced by Chisso Corp., having the following formula:

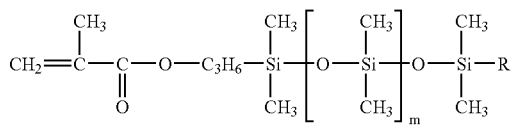

and an average molecular weight of 5,000) and 9 g of tert-butylperoxy-2-ethyl hexanoate (PBO) as polymerization initiator was added dropwise over a period of 180 minutes. After the completion of this dropwise addition, the mixture was maintained at the same temperature for 3 hours and then cooled to obtain a milky white dispersed polymer solution with a solid content of 60.2% and a viscosity of 3.6 Ps.

The weight-average molecular weight of the thus obtained dispersed polymer, as determined by GPC, was 31,000. The average particle size of the dispersion, as determined by using a laser doppler/frequency analysis type particle size analyzer (UPA150 mfd. by Nikkisoh Ltd.), was 0.27 μm.

EXAMPLE 2

According to the procedure of Example 1, 400 g of KF-995 was added to the reactor and heated and maintained at 120° C., to which a mixture of 270 g of methyl methacrylate, 250 g of butyl acrylate (BA), 40 g of 2-hydroxyethyl methacrylate (2HEMA), 40 g of FM-0725 (having the same structure as FM-0721 with an average molecular weight of 10,000, produced by Chisso Corp.) and 9 g of tert-butylperoxy-2-ethyl hexanoate was added dropwise over a period of 180 minutes. The mixture was maintained at the same temperature for 3 hours and then cooled to obtain a milky white dispersed polymer solution with a solid content of 60.1% and a viscosity of 5.3 Ps.

The weight-average molecular weight of the resulting dispersed polymer was 28,000, and its average particle size was 0.28 μm.

EXAMPLE 3

According to the procedure of Example 1, 400 g of KF-994 (decamethylcyclopentanesiloxane produced by Shin-Etsu Chemical Industries Co., Ltd.) was added to the reactor instead of KF-995, to which a mixture of 50 g of methyl methacrylate, 460 g of butyl methacrylate (BMA), 30 g of butyl acrylate, 60 g of FM-0721 and 4 g of tert-butylperoxy-2-ethyl hexanoate was added dropwise at 110° C. over a period of 180 minutes. The mixture was maintained at the same temperature for another 180 minutes and then cooled to obtain a milky white dispersed polymer solution with a solid content of 60.2% and a viscosity of 4.3 Ps.

The weight-average molecular weight of the dispersed polymer was 52,000 and its average particle size was 0.30 μm.

Comparative Example 1

400 g of toluene (TOL) was added to a reactor equipped with a thermometer, a reflux condenser, a stirrer and a dropping funnel, and after replacing the reactor atmosphere with nitrogen gas, TOL was heated and maintained at 110° C. To this, a mixture of 336 g of methyl methacrylatel, 224 parts of 2-ethylhexyl acrylate, 40 g of a commercial silicone macromonomer FM-0721 and 9 g of tert-butylperoxy-2-ethyl hexanoate as polymerization initiator was added dropwise over a period of 180 minutes. After completion of this dropwise addition, the mixture was maintained at the same temperature for 3 hours and then cooled to obtain a transparent polymer solution with a solid content of 60.3% and a viscosity of 52.7 Ps.

The weight-average molecular weight of the obtained polymer was 29,000.

Comparative Example 2

According to the procedure of Comparative Example 1, 500 g of toluene was added to the reactor and heated and maintained at 110° C., to which a mixture of 220 g of methyl methacrylate, 90 parts of 2-ethylhexyl acrylate, 150 g of FM-0721 and 9 g of tert-butylperoxy-2-ethyl hexanoate as polymerization initiator was added dropwise over a period of 180 minutes. After completion of the dropwise addition, the mixture was maintained at the same temperature for 3 hours and then cooled to obtain a translucent polymer solution with a solid content of 50.2% and a viscosity of 23.4 Ps. The weight-average molecular weight of the resulting polymer was 32,000.

100 g of the resulting polymer was poured into 1,000 g of methanol to let the polymer precipitate. The precipitate was separated and dried to obtain the solid polymer.

Comparative Example 3

According to the procedure of Example 1, 500 g of KF-995 was added to the reactor and heated and maintained at 110° C., to which a mixture of 220 g of methyl methacrylate, 90 g of butyl methacrylate, 150 g of FM-0721 and 9 g of tert-butylperoxy-2-ethyl hexanoate was added dropwise over a period of 180 minutes. After this, the mixture was maintained at the same temperature for 3 hours and then cooled to obtain a milky white dispersed polymer solution with a solid content of 50.2% and a viscosity of 2.5 Ps.

The weight-average molecular weight of the dispersed polymer was 32,000 and its average particle size was 0.25 μm.

Comparative Example 4

According to the procedure of Example 1, 400 g of KF-995 was added to the reactor and heated and maintained at 120° C., to which a mixture of 480 g of methyl methacrylate, 60 g of styrene (ST), 20 g of butyl acrylate, 40 g of FM-0721 and 9 g of tert-butylperoxy-2-ethyl hexanoate was added dropwise over a period of 180 minutes. The mixture was maintained at the same temperature for another 3 hours and then cooled to obtain a milky white dispersed polymer solution with a solid content of 60.2% and a viscosity of 2.8 Ps. The weight-average molecular weight of the dispersed polymer was 29,000 and its average particle size was 0.26 μm.

Properties of the polymers obtained in Examples 1 to 3 and Comparative Examples 1 to 4 are shown in Tables 1 and 2.

TABLE 1

Polymerization conditions of the dispersed polymer in silicone oil

|  |  | Example | | | Comp. Example | | | |
|---|---|---|---|---|---|---|---|---|
|  |  | 1 | 2 | 3 | 1 | 2 | 3 | 4 |
| Solvent (g) | KF-995 | 400 | 400 |  |  |  | 500 | 400 |
|  | KF-994 |  |  | 400 |  |  |  |  |
|  | TOL |  |  |  | 400 | 500 |  |  |

TABLE 1-continued

Polymerization conditions of the dispersed polymer in silicone oil

|  |  | Example | | | Comp. Example | | | |
|---|---|---|---|---|---|---|---|---|
|  |  | 1 | 2 | 3 | 1 | 2 | 3 | 4 |
| Silicone macromonomer (g) | FM-0721 | 40 |  | 60 | 40 | 150 | 150 | 40 |
|  | FM-0725 |  | 40 |  |  |  |  |  |
| Monomers (g) | ST |  |  |  |  |  |  | 60 |
|  | MMA | 336 | 270 | 50 | 336 | 220 | 220 | 480 |
|  | BMA |  |  | 460 |  |  |  |  |
|  | BA |  | 250 | 30 |  |  |  | 20 |
|  | 2EHA | 224 |  |  | 224 | 90 | 90 |  |
|  | 2HEMA |  | 40 |  |  |  |  |  |
| Catalyst (g) | PBO | 9 | 8 | 4 | 9 | 9 | 9 | 9 |
| Reaction temperature (° C.) |  | 120 | 120 | 110 | 110 | 110 | 110 | 120 |

TABLE 2

Properties of the dispersed polymer in silicone oil

|  | Example | | | Comp. Example | | | |
|---|---|---|---|---|---|---|---|
|  | 1 | 2 | 3 | 1 | 2 | 3 | 4 |
| Solid content (wt. %) | 60.2 | 60.1 | 60.2 | 60.3 | 50.2 | 50.2 | 60.2 |
| Viscosity (ps) | 3.6 | 5.3 | 4.3 | 52.7 | 23.4 | 2.5 | 2.8 |
| Average particle size (μm) | 0.27 | 0.29 | 0.30 | — | — | 0.25 | 0.26 |
| Weight-average molecular weight | 31000 | 25000 | 52000 | 29000 | 32000 | 32000 | 29000 |
| Tg of acryl moiety (° C.) | 8.1 | 8.7 | 19.7 | 8.1 | 27.3 | 27.3 | 94.5 |
| Content of silicone macromonomer (wt. %) | 7.1 | 10 | 7.1 | 7.1 | 30 | 30 | 7.1 |

Performance of the obtained polymers was examined by the following test procedures and evaluated according to the evaluation criteria as shown below. Results are shown in Table 3.

Test Procedures (1) Transparency

The dispersion to be tested was applied on a transparent glass plate to form a film at 20° C. and 65% RH so that the dry film thickness is 20 μm, and the degree of cloudiness of the resulting film was visually determined.

(2) Water Resistance

The dispersed resin solution was applied on a clean fluorine film to form a coating film so that the dry film thickness is 20 μm. After drying, the coating film was stripped off and immersed in tap water for 3 days, and then the change of status of the coating film was visually observed.

(3) Oil Resistance

A coating film was formed in the same way as in the method of the above (2) and immersed in indodecane for 24 hours, and the change of status of the coating film was visually observed.

(4) Adhesion to the Skin

A few drops of the dispersion were applied on the back of a hand, and after drying, the formed film was rubbed with fingers. Adhesion to the skin was judged by the difficulty in removing the film from the skin.

(5) Applicability

Applicability of the dispersion was determined by the "hitch" in spreading the dispersion on the back of a hand with fingers until it was dried to form a film.

(6) Conformability to Skin

This was determined by the sense of stretch on the skin given by the film formed according to the above (5) after it was dried.

Criterion for Evaluation

TABLE 3

Evaluation results

|  | Example | | | Comp. Example | | | |
|---|---|---|---|---|---|---|---|
|  | 1 | 2 | 3 | 1 | 2 | 3 | 4 |
| Coating film quality |  |  |  |  |  |  |  |
| Transparency | ○ | ○ | ○ | ○ | ○ | ○ | — |
| Water resistance | ○ | ○ | ○ | ○ | ○ | ○ | — |
| Oil resistance | ○ | ○ | ○ | ○ | ○ | ○ | — |
| Adhesion | ○ | ○ | ○ | ○ | ○ | ○ | X |
| Use characteristics |  |  |  |  |  |  |  |
| Applicability | ⊙ | ⊙ | ⊙ | X | X | Δ | ⊙ |
| Conformability to skin | ⊙ | ⊙ | ⊙ | X | X | Δ | — |

⊙: Very good; ○: Good; Δ: Rather bad; X: Bad

Preparation of Cosmetics (Examples of Compounding in Liquid Foundation

EXAMPLE 4

The following components (1) to (10) were mixed and dispersed uniformly by a sand grinder to obtain a liquid foundation:

| | |
|---|---|
| (1) Dispersed polymer in silicone oil (Example 1) | 45.0 g |
| (2) Dimethylpolysiloxane | 5.3 g |
| (3) Isoparaffin (Isopar K*) | 9.0 g |
| (4) Titanium oxide | 19.3 g |
| (5) Red iron oxide | 1.2 g |
| (6) Yellow iron oxide | 2.7 g |
| (7) Black iron oxide | 0.9 g |
| (8) Mica | 12.0 g |
| (9) Talc | 4.5 g |
| (10) Perfume | 0.1 g |

*Produced by Exxon Chemical Co., Ltd.

Comparative Example 5

The following components (1) to (5) were mixed and dissolved under heating, then the remaining components (6) to (11) were added, and these components were dispersed uniformly by a roll mill to obtain a liquid foundation:

| | |
|---|---|
| (1) Solid polymer obtained in Comparative Example 2 | 15.0 g |
| (2) Dimethylpolysiloxane | 9.0 g |
| (3) Decamethylcyclopentasiloxane | 6.0 g |
| (4) Isoparaffin (Isopar K) | 39.8 g |
| (5) Titanium oxide | 12.9 g |
| (6) Red iron oxide | 0.8 g |
| (7) Yellow iron oxide | 1.8 g |
| (8) Black iron oxide | 0.6 g |
| (9) Mica | 8.0 g |
| (10) Talc | 3.0 g |
| (11) Perfume | 0.1 g |

Results of evaluation of the liquid foundations obtained in Example 4 and Comparative Example 5 are shown in Table 4.

TABLE 4

| Evaluation results | | |
|---|---|---|
| | Example 4 | Comp. Example 5 |
| Spread | ◎ | Δ |
| Lightweight feeling | ○ | ○ |
| Absence of uncomfortable feeling | ◎ | Δ |
| Lasting make-up | ○ | ○ |

Criterion for Evaluation
◎: Very good; ○: good; Δ: Rather bad; X: Bad

What is claimed is:

1. A process for producing a liquid non-aqueous dispersion having a copolymer dispersed in a silicone oil, which comprises copolymerizing (A) 1 to 20% by weight of at least one radical polymerizable macromonomer containing dimethyl polysiloxane, the macromonomer (A) being represented by the formula (1):

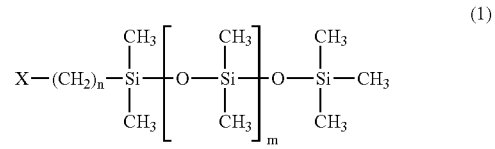

(wherein X represents a radical polymerizable group, n is an integer of 1 to 10, and m is an integer of 3 to 300), and (B) 99 to 80% by weight of at least one radical copolymerizable monomer with said macromonomer (A), the monomer (B) comprising at least one (meth) acrylate monomer and optionally at least one vinyl monomer, by subjecting said monomers to one-step polymerization in a silicone oil in the presence of a radical polymerization initiator without a dispersion stabilizer.

2. The process according to claim 1, wherein the amount of the radical polymerization initiator is 0.01 to 5% by weight based on the whole amount of the monomers.

* * * * *